(12) United States Patent
Glerum et al.

(10) Patent No.: US 11,826,262 B2
(45) Date of Patent: Nov. 28, 2023

(54) PEDICLE-BASED INTRADISCAL FIXATION DEVICES AND METHODS

(71) Applicant: GLOBUS MEDICAL, INC., Audubon, PA (US)

(72) Inventors: Chad Glerum, Pennsburg, PA (US); Mark Weiman, Downingtown, PA (US); Tyler Hessler, Phoenixville, PA (US); Albert Hill, Richboro, PA (US); Myles Sullivan, Philadelphia, PA (US)

(73) Assignee: Globus Medical Inc., Audubon, PA (US)

( * ) Notice: Subject to any disclaimer, the term of this patent is extended or adjusted under 35 U.S.C. 154(b) by 355 days.

(21) Appl. No.: 16/842,916

(22) Filed: Apr. 8, 2020

(65) Prior Publication Data
US 2021/0307923 A1    Oct. 7, 2021

Related U.S. Application Data

(63) Continuation of application No. 16/842,285, filed on Apr. 7, 2020.

(51) Int. Cl.
*A61B 17/70* (2006.01)
*A61F 2/44* (2006.01)
*A61B 17/56* (2006.01)
*A61F 2/30* (2006.01)

(52) U.S. Cl.
CPC .......... *A61F 2/446* (2013.01); *A61B 17/7032* (2013.01); *A61B 2017/564* (2013.01); *A61F 2002/30131* (2013.01); *A61F 2002/30405* (2013.01); *A61F 2002/30841* (2013.01); *A61F 2002/30886* (2013.01)

(58) Field of Classification Search
None
See application file for complete search history.

(56) References Cited

U.S. PATENT DOCUMENTS

| 7,909,871 B2 * | 3/2011 | Abdou | A61B 17/70 606/264 |
|---|---|---|---|
| 10,258,394 B2 * | 4/2019 | Harshman | A61B 17/7266 |
| 2004/0210227 A1 * | 10/2004 | Trail | A61B 17/8635 606/328 |
| 2005/0033292 A1 * | 2/2005 | Teitelbaum | A61B 17/1617 606/53 |
| 2005/0216018 A1 * | 9/2005 | Sennett | A61B 17/1671 606/79 |

(Continued)

FOREIGN PATENT DOCUMENTS

| FR | 3054788 B1 | 2/2018 |
|---|---|---|
| JP | 2008539029 A | 11/2008 |

(Continued)

*Primary Examiner* — Jan Christopher L Merene

(57) ABSTRACT

Pedicle-based intradiscal fixation devices, systems, instruments, and methods thereof. An implant for stabilizing an inferior vertebra and a superior vertebra may include a first member and a second member moveably connected to the first member. The implant may have a first, initial insertion orientation and a second, final implantation orientation different from the first, initial insertion orientation. The first member may be configured to be inserted through a pedicle of the inferior vertebra and the second member may be configured to engage bone of the superior vertebra in the second, final implantation orientation.

6 Claims, 15 Drawing Sheets

(56) References Cited

U.S. PATENT DOCUMENTS

| | | | |
|---|---|---|---|
| 2008/0033432 A1* | 2/2008 | McGraw | A61B 17/7098 606/86 A |
| 2010/0016903 A1* | 1/2010 | Matityahu | A61B 17/866 606/301 |
| 2010/0082033 A1* | 4/2010 | Germain | A61B 17/3472 606/86 R |
| 2011/0144703 A1* | 6/2011 | Krause | A61B 17/869 606/309 |
| 2011/0282387 A1 | 11/2011 | Suh et al. | |
| 2014/0163624 A1 | 6/2014 | Siegal et al. | |
| 2014/0277162 A1* | 9/2014 | Kostuik | A61B 17/1671 606/279 |
| 2015/0257800 A1* | 9/2015 | Harshman | A61B 17/1717 606/62 |
| 2016/0310190 A1 | 10/2016 | Blohm et al. | |
| 2020/0030013 A1 | 1/2020 | Blohm et al. | |
| 2021/0386465 A1* | 12/2021 | Thaler | A61B 17/7208 |

FOREIGN PATENT DOCUMENTS

| | | | |
|---|---|---|---|
| JP | 2018519977 A | 7/2018 | |
| WO | WO-2018024617 A1 * | 2/2018 | A61B 17/70 |

\* cited by examiner

PEDICLE-BASED INTRADISCAL FIXATION DEVICES AND METHODS

CROSS REFERENCE TO RELATED APPLICATIONS

This application is a continuation application claiming priority to U.S. patent application Ser. No. 16/842,285 filed on Apr. 7, 2020, which is incorporated in its entirety herein.

FIELD OF THE INVENTION

The present disclosure relates to surgical devices, and more particularly, to pedicle-based intradiscal fixation devices and associated methods.

BACKGROUND OF THE INVENTION

Common procedures for handling pain associated with intervertebral discs that have become degenerated due to various factors such as trauma or aging may include the use of pedicle screw fixation and/or intervertebral fusion for fusing one or more adjacent vertebral bodies. Generally, bilateral pedicle screw fixation, for example, with a rod construct, may be used to treat degenerative disc disease and a multitude of other spine pathologies as a standard of treatment to stabilize two or more adjacent vertebral bodies, for example, as an adjunct to spinal fusion.

Unfortunately, a number of iatrogenic pathologies are associated with pedicle screw fixation including, but not limited to, misplacement of screws, muscle/ligamentous disruption during insertion, adjacent segment disease due to superior adjacent facet violation by the inferior pedicle screw construct, increased procedural time, and/or instrumentation failure. There exists a clinical need for a fixation system and method that reduces the iatrogenic effects of a bilateral pedicle screw construct from a posterior approach while stabilizing two adjacent vertebral bodies that may be used as an adjunct to spinal fusion.

SUMMARY OF THE INVENTION

In accordance with the application, pedicle-based devices, systems, and methods are provided. In particular, pedicle-based intradiscal fixation devices are provided, which may be used as a standalone device or may be used in conjunction with a traditional interbody fixation device. The method of fixation may include inserting the device through the pedicle of an inferior vertebra, into the vertebral body of the inferior vertebra and securing the device to the vertebral body of the adjacent superior vertebra. The pedicle-based intradiscal fixation devices and methods described herein may improve access-related morbidity while providing sufficient stabilization force for spinal fusion.

According to one embodiment, an implant for stabilizing an inferior vertebra and a superior vertebra includes a first member and a second member connected to the first member. The implant has a first, initial insertion orientation and a second, final implantation orientation different from the first, initial insertion orientation. The first member is configured to be inserted through a pedicle of the inferior vertebra and the second member is configured to engage bone of the superior vertebra in the second, final implantation orientation.

According to another embodiment, methods of intradiscal fixation are provided. A method for stabilizing an inferior vertebra and a superior vertebra may include: posteriorly accessing a spine of a patient; inserting an implant having a first member and a second member into a pedicle of the inferior vertebra in a first, initial orientation; inserting the first member of the implant into a vertebral body of the inferior vertebra; and modifying the implant into a second, final implantation orientation and inserting the second member of the implant into a vertebral body of the superior vertebra, wherein the implant traverses a disc or disc space between the inferior and superior vertebrae, and the second, final implantation orientation thereby fixates the inferior and superior vertebrae.

According to one embodiment, the implant may include a pedicle screw, a housing affixed to the pedicle screw, and an anchor moveably connected to the housing. The implant has a collapsed position whereby the anchor is positioned close to the pedicle screw, and the implant has an extended position whereby the anchor is moved away from or extended from the pedicle screw. The pedicle screw is configured to be inserted through a pedicle of the inferior vertebra in the collapsed position, and the anchor is configured to engage bone of the superior vertebra in the extended position.

The pedicle screw implant may include one or more of the of the following features. The pedicle screw may have a proximal end including a recess configured to receive an instrument for inserting the pedicle screw and a distal end configured to be inserted into the pedicle of the inferior vertebra. The pedicle screw may include one or more threads configured to engage bone. The housing may include a first portion configured to receive the pedicle screw and a second portion configured to retain the anchor therein. The anchor may be configured to move, pivot, or articulate relative to the pedicle screw. The anchor may have a proximal end configured to be received in the housing and a distal end configured to be inserted into a vertebral body of the superior vertebra in the extended position. The anchor may be curved between the proximal and distal ends. The anchor may be generally positioned perpendicular to the pedicle screw in the extended position. The anchor may include one or more tracks configured to engage corresponding tracks within the second portion of the housing, and thereby allow for movement of the anchor between the collapsed and extended positions.

According to another embodiment, the implant may include a curved outer tube and a curved inner tube positionable within the outer tube. The implant has a collapsed position whereby the inner tube is positioned inside the outer tube, and the implant has an extended position whereby the inner tube extends from the outer tube. The outer tube is configured to be inserted through a pedicle of the inferior vertebra in the collapsed position, and the inner tube is configured to engage bone of the superior vertebra in the extended position.

The tube implant may include one or more of the of the following features. The inner tube may include one or more ribs extending along the length of the tube configured to engage bone. The outer and inner tubes may be hollow and may be configured to receive bone cement therethrough. The implant may further include a separate segmented tube configured to advance the inner tube and stabilize the outer tube. The segmented tube may include a plurality of articulating links. Each of the links may include a joint, such as a ball and a socket configured to receive the ball of an adjacent link. The segmented tube may be encapsulated by the outer tube in the extended position.

According to another embodiment, the implant may include a screw portion and an anchor portion moveably coupled to the screw portion. The implant has a collapsed position whereby the anchor portion is positioned substantially in line with the screw portion, and the implant has an extended position whereby the anchor portion is extended away from the screw portion. The screw portion is configured to be inserted through a pedicle of the inferior vertebra in the collapsed position, and the anchor portion is configured to engage bone of the superior vertebra in the extended position.

The anchor implant may include one or more of the of the following features. The implant may further include a rod portion receivable in the screw portion. The implant may also include a push rod connected to a distal end of the screw portion by a first pin and connected to the anchor portion by a second pin. When the screw portion moves forward along the rod portion, the push rod may push forward and slide the anchor portion outward into the extended position. The rod portion may include one or more tracks configured to mate with corresponding tracks along the anchor portion, thereby facilitating movement of the anchor portion relative to the screw portion.

According to another embodiment, the implant includes a curved nail and a flexible screw moveable along the length of the nail. The implant has a first position whereby the nail is configured to be inserted into a pedicle of the inferior vertebra, a vertebral body of the inferior vertebra, and a vertebral body of the superior. The implant has a final position whereby the screw is inserted over the nail to rigidly lock the nail and screw together and provide resistance to pullout. The flexible screw may include one or more threads, and the flexible screw may have an open helical design with gaps between crests of the one or more threads.

Also provided are kits including pedicle-based intradiscal fixation devices of varying types and sizes, interbody fusion devices of varying types and sizes, rods, fasteners or anchors, k-wires, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Bilateral pedicle screw fixation has been used to treat degenerative disc disease and other spine pathologies. However, a number of iatrogenic pathologies are associated with pedicle screw fixation. Thus, there is a need for a fixation method that reduces the iatrogenic effects of a bilateral pedicle screw construct from a posterior approach while stabilizing the two adjacent vertebral bodies. According to one embodiment, an inferior pedicle-based intradiscal fixation method may be used in a standalone method or in conjunction with a traditional interbody fixation device. The system may improve access-related morbidity while providing sufficient stabilization force for spinal fusion. Accordingly, embodiments of the present application are generally directed to devices, systems, and methods for pedicle-based intradiscal fixation of two adjacent vertebrae. The terms device, fixation device, and implant may be used interchangeably herein.

Figure 1:
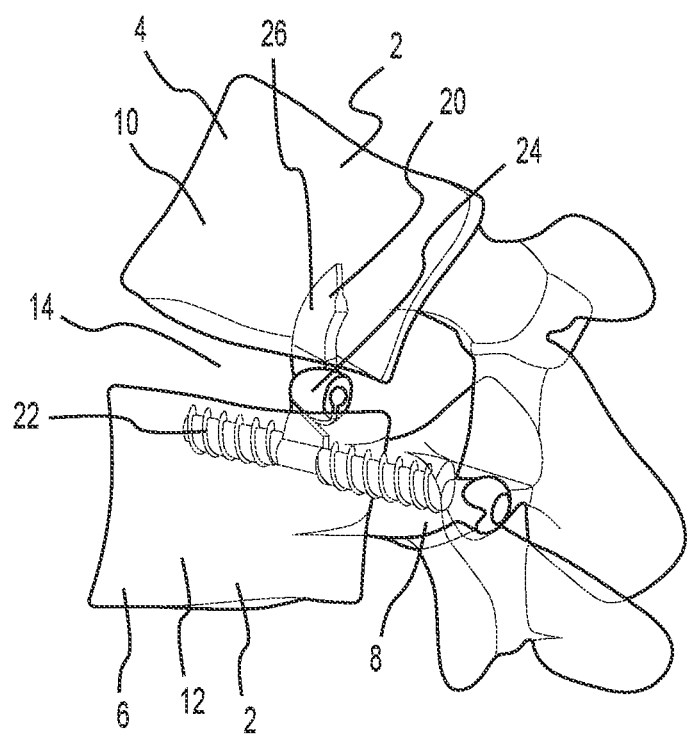
FIG. 1 is a lateral view of two adjacent vertebrae with a pedicle-based intradiscal fixation device implanted through the pedicle of the inferior vertebra and engaged with the vertebral body of the superior vertebra according to one embodiment.
Figure 2:
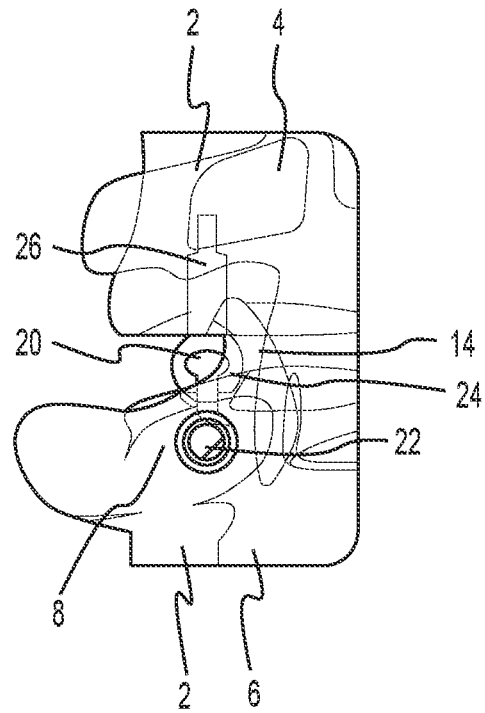
FIG. 2 is a posterior view of the vertebrae and pedicle-based intradiscal fixation device of FIG. 1.

Referring now to FIGS. 1 and 2, a pedicle-based intradiscal fixation device 20 according to one embodiment is shown implanted into two adjacent vertebrae 2, namely, a superior vertebra 4 and an inferior vertebra 6. The method of fixation may include, for example, accessing the spine from the posterior and inserting the device 20 into the pedicle 8 of the inferior vertebra 6. If necessary, bone may be removed from the inferior pedicle 8 and/or the vertebral body 12 in order to facilitate placement of the device 20. The device 20 may be further advanced into the vertebral body 12 of the inferior vertebra 6. As shown, the device 20 may be angled or directed toward the superior of the inferior body 6, but it is also envisioned that the location and orientation of the device 20 may be selected by a surgeon. The device 20 may be configured to be inserted and secured to the vertebral body 10 of the adjacent superior vertebra 4. Thus, the device 20 may traverse the disc and/or disc space 14 between the two vertebrae 2. In this manner, the device 20 may be configured to be implanted into both vertebrae 2 from a posterior approach, thereby allowing for fusion of the adjacent vertebrae 2. One or more pedicle-based devices 20 may be used alone or in conjunction with a traditional interbody fusion device. Although the method is shown with respect to a single inferior pedicle 8, it will be appreciated that the other inferior pedicle (not shown) may also receive the same or a similar device. It will also be appreciated that the same or similar devices may also be used on adjacent or other levels.

Figure 3:
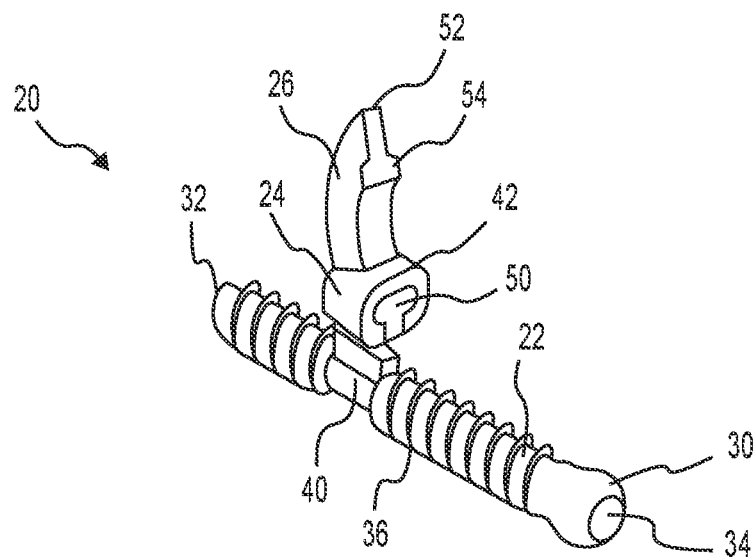
FIG. 3 is a perspective view of the pedicle-based intradiscal fixation device of FIG. 1.
Figure 4:
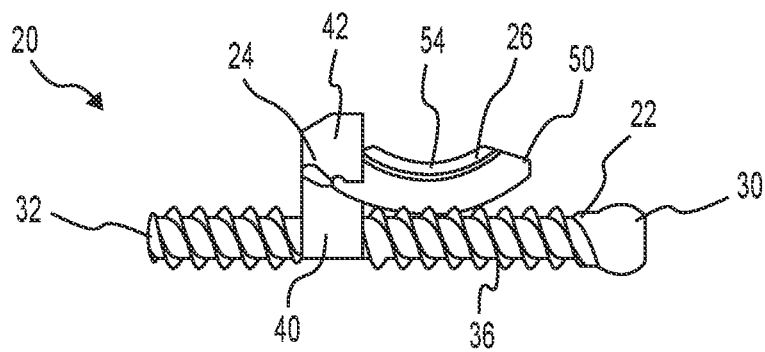
FIG. 4 is a side view of the pedicle-based intradiscal fixation device of FIG. 3 in a collapsed position.
Figure 5:
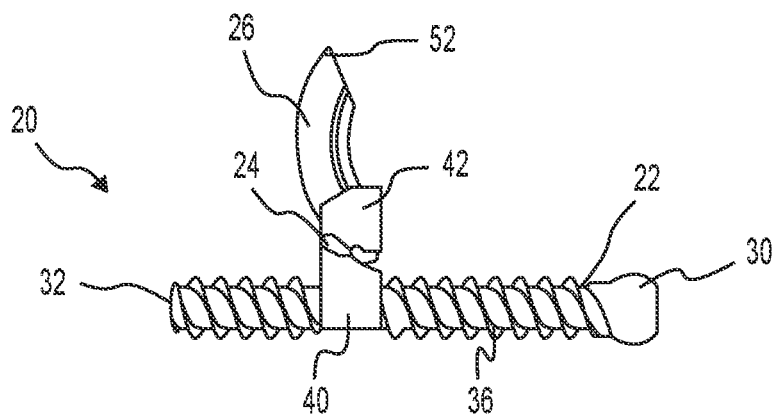
FIG. 5 is a side view of the pedicle-based intradiscal fixation device of FIG. 3 in an extended position.

Turning now to FIGS. 3-5, the pedicle-based intradiscal fixation device 20 is shown in more detail. The pedicle-based implant 20 may include a pedicle screw 22, a housing 24 affixed to the pedicle screw 22, and an anchor 26 moveably connected to the housing 24. As best seen in FIG. 4, the implant 20 has a collapsed configuration whereby the anchor 26 is positioned close to the pedicle screw 22, thereby allowing the implant 20 to be inserted into the pedicle 8 of the inferior vertebra 6, for example, in a minimally invasive manner. As shown in FIG. 5, once inserted in the inferior vertebra 6, the implant 20 has an expanded or extended configuration whereby the anchor 26 is moved away from the pedicle screw 22, thereby allowing for the anchor 26 to be inserted into the superior vertebra 4.

The pedicle screw 22 may have a body extending from a first end 30 to a second end 32. The first end 30 may be a proximal end and may include a recess 34 configured to receive an instrument for inserting the pedicle screw 22. The first end 30 may have an enlarged head portion or may be otherwise configured (e.g., headless). The second end 32 may be a distal end configured to be inserted into the pedicle 8 of the inferior vertebra 6. The second end 32 may have a distal tip that is blunt, pointed, or otherwise configured to engage bone. The body of the pedicle screw 22 may include one or more threads 36 along the entire length of the shaft or a portion thereof. The thread 36 may have a suitable angle, lead, pitch, etc. to enhance insertion and/or engagement with the bone. Although a pedicle screw 22 is exemplified in this embodiment, it will be appreciated that the pedicle screw 22 could be substituted with a bone anchor, nail, or other fixation device.

The housing 24 may be affixed to the pedicle screw 22. The housing 24 may include a first portion 40 configured to receive the pedicle screw 22. For example, the first portion 40 may have an opening extending therethrough configured to receive the shaft of the pedicle screw 22 in a position where the threads 36 are absent. The outer surface of the first portion 40 may be dimensioned to be smaller than the major diameter of the threads 36. The housing 24 may be positioned centrally along the pedicle screw 22 or more towards the distal end 32. The housing 24 may include a second portion 42 configured to retain the anchor 26. The second portion 42 may include an opening configured to receive the anchor 26, which is configured to move, slide, pivot, or articulate the anchor 26 relative to the screw 22.

The anchor 26 may have a body extending from a first end 50 to a second end 52. The first end 50 may be a proximal end and the second end 52 may be a distal end configured to be inserted into the vertebral body 10 of the superior vertebra 4. The second end 52 may have a distal tip that is sharp, pointed, or otherwise configured to engage bone. The body of the anchor 26 may include one or more tracks 54 configured to engage corresponding tracks within the opening of the second portion 42 of the housing 24. The one more mating tracks 54 may be provided to allow for movement of the anchor 26 between the collapsed and extended positions. For example, in the collapsed position, shown in FIG. 4, the distal end 52 of the anchor 26 may be received in the housing 24, and after a force is applied to the proximal end 50 of the anchor 26, the anchor 26 moves into the extended position, shown in FIG. 5, such that the proximal end 50 of the anchor 26 is received in the housing 24. In the extended position, the anchor 26 may be generally positioned perpendicular to the pedicle screw 22 or the anchor 26 may be angled or otherwise oriented to engage the vertebral body 10 of the superior vertebra 4. It is also envisioned that the anchor 26 could pivot in the housing 24 about a joint, such as a pin joint or hinge joint. Although a single anchor 26 is depicted in this embodiment, it will be appreciated that additional anchors 26 could be received in the housing 24. Multiple anchor geometries may be used to facilitate stability, for example, one or more anchors 26 may be inserted into the anchor housing 24 with orientation variances in up to three planes.

Figure 6:
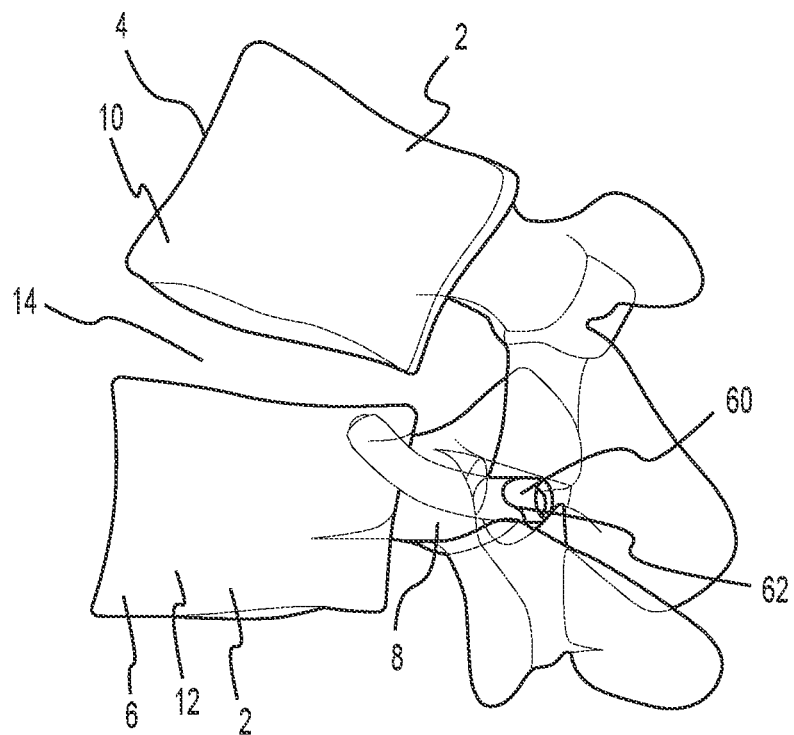
FIG. 6 is a lateral view of two adjacent vertebrae with a pedicle-based intradiscal fixation device in a collapsed position implanted through the pedicle of the inferior verterbra according to one embodiment.
Figure 7:
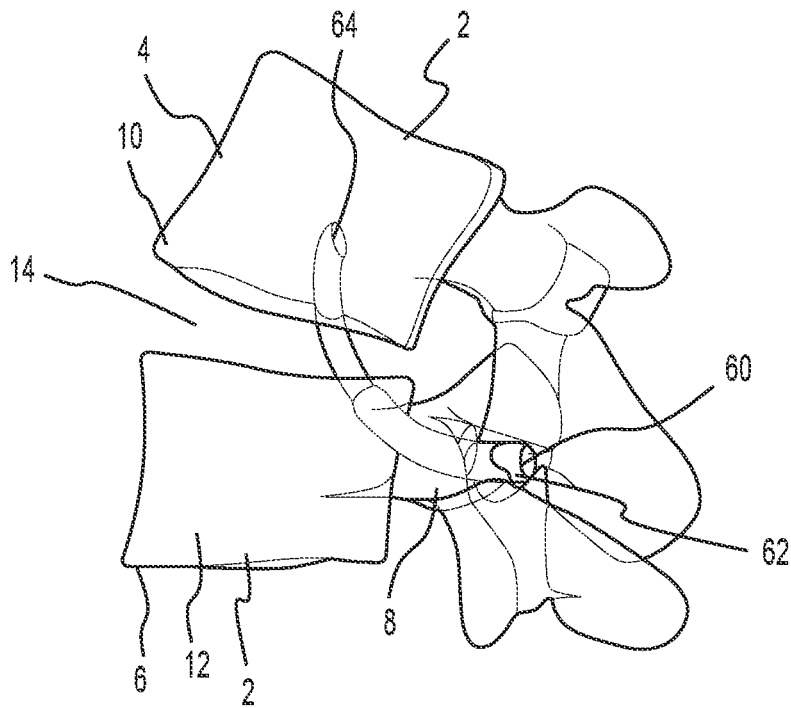
FIG. 7 is a lateral view of two adjacent vertebrae and the pedicle-based intradiscal fixation device of FIG. 6 with the device in an extended position and further implanted into the vertebral body of the superior vertebra.

Referring now to FIGS. 6 and 7, a pedicle-based intradiscal fixation device 60 according to another embodiment is shown. In FIG. 6, the pedicle-based implant 60 is implanted into the inferior vertebra 6 in a collapsed position. In FIG. 7, the pedicle-based implant is deployed to an expanded or extended position such that the implant 60 is implanted into the vertebral body 10 of the superior vertebra 4. The method of fixation may be similar to the method described for device 20. For example, the spine may be accessed posteriorly and the device 60 may be inserted into the pedicle 8 of the inferior vertebra 6. If necessary, bone may be removed from the inferior pedicle 8 and/or the vertebral body 12 in order to facilitate placement of the device 60. The device 60 may be further advanced into the vertebral body 12 of the inferior vertebra 6. The device 60 may be configured to be inserted and secured to the vertebral body 10 of the adjacent superior vertebra 4. Thus, the device 60 may traverse the disc and/or disc space 14 between the two vertebrae 2. If desired, cement may be injected through the implant 60 to rigidly fixate the implant 60 to the superior vertebral body 10.

Figure 8:
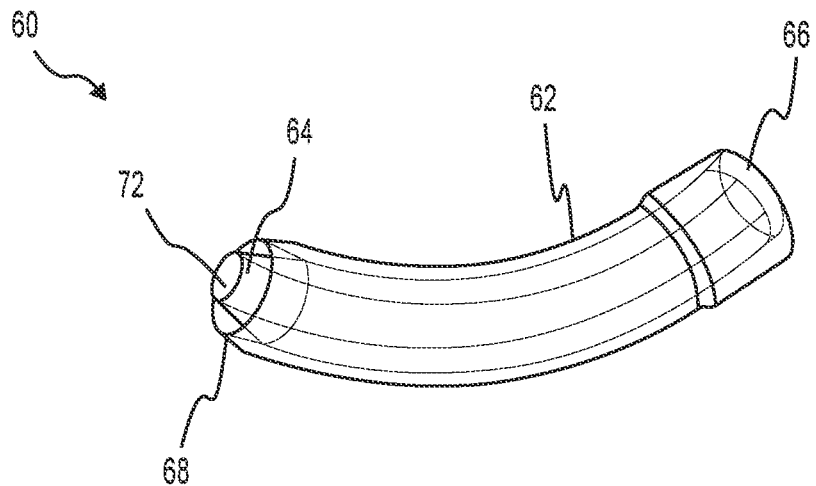
FIG. 8 is a perspective view of the pedicle-based intradiscal fixation device of FIG. 6 in a collapsed position.
Figure 9:
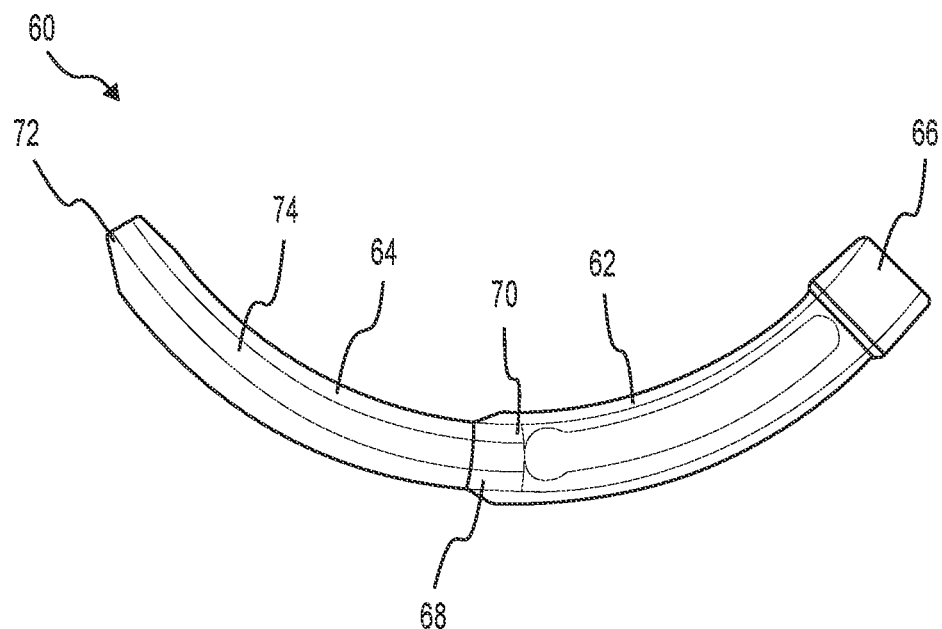
FIG. 9 is a perspective view of the pedicle-based intradiscal fixation device of FIG. 8 in an extended position.

Turning now to FIGS. 8 and 9, the pedicle-based intradiscal fixation device 60 is shown in more detail. The pedicle-based implant 60 may include two or more concentric tubes. In particular, the implant 60 may include a first tube or outer tube 62 and a second tube or inner tube 64 positionable within the outer tube 62. As best seen in FIG. 8, the implant 60 has a collapsed configuration whereby the inner tube 64 is positioned inside the outer tube 62, thereby allowing the implant 60 to be inserted into the pedicle 8 of the inferior vertebra 6, for example, in a minimally invasive manner. As shown in FIG. 9, once inserted in the inferior vertebra 6, the implant 60 has an expanded or extended configuration whereby the inner tube 64 extends from the outer tube 62, thereby allowing for the inner tube 64 to be inserted into the superior vertebra 4.

The first tube or outer tube 62 may have a body extending from a first end 66 to a second end 68. The first end 66 may be a proximal end and the second end 68 may be a distal end configured to be inserted into the pedicle 8 of the inferior vertebra 6. The outer tube 62 may be generally hollow and may be curved along its length. The second tube or inner tube 64 may have a body extending from a first end 70 to a second end 72. The first end 70 may be a proximal end and the second end 72 may be a distal end configured to be inserted into the vertebral body 10 of the superior vertebra 4. The second end 72 may have a distal tip that is blunt, sharp, or otherwise configured to engage bone. The second tube 64 may also have one or more ribs 74 extending along the length or a portion thereof of the tube 64 configured to engage bone. The inner tube 64 may be generally hollow and may be curved along its length. In an alternative embodiment, the inner tube 64 may be an anchor, keel, or other fixation device and is not necessarily hollow throughout.

In one embodiment, the implant 60 may be installed as follows. The concentric curved tubes 62, 64 may be inserted into the pedicle 8 of the inferior vertebra 6. An instrument drives the inner concentric tube 64 into the superior vertebral body 10. Bone cement, such as polymethyl methacrylate (PMMA) or a suitable self-setting orthopedic cement composition, may be injected through the concentric curved tubes 62, 64 to rigidly fixate the implant assembly to the superior vertebral body 10. In addition or in the alternative, bone cement may be inserted through the superior vertebral body pedicle to rigidly fixate the implant assembly to the superior vertebral body 10.

Figure 10:
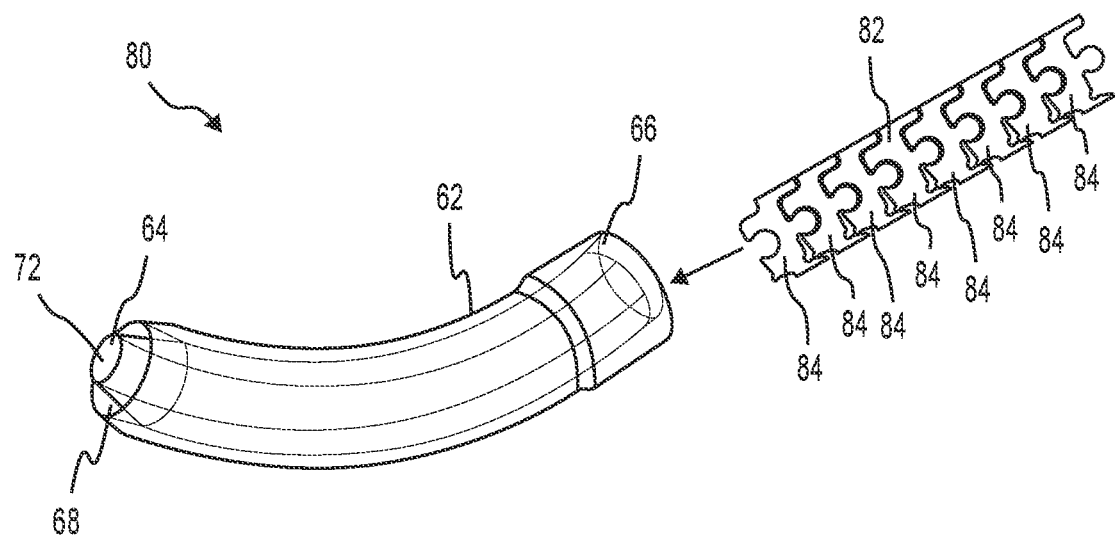
FIG. 10 is an exploded perspective view of a pedicle-based intradiscal fixation device according to another embodiment with the device in a collapsed position and a separate segmented device.
Figure 11:
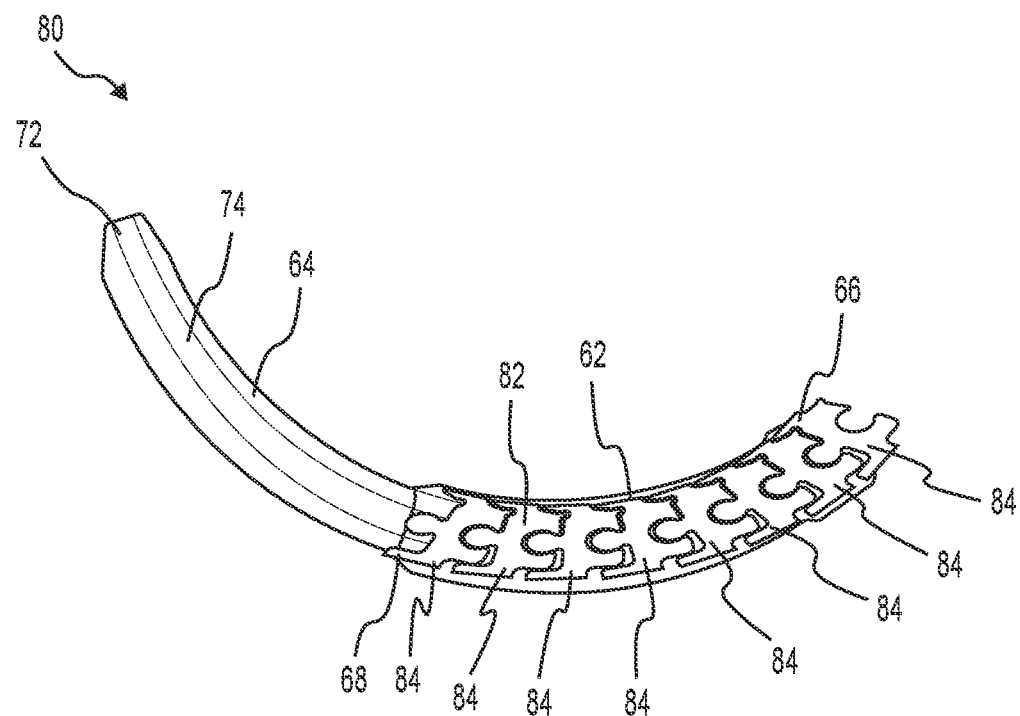
FIG. 11 is the pedicle-based intradiscal fixation device of FIG. 10 with the segmented device inserted into the outer tube to advance the inner member to the extended position.

Referring now to FIGS. 10 and 11, a pedicle-based intradiscal fixation device 80 according to another embodiment is shown. The concentric curved tubes 62, 64 may be the same as described for implant 60 with a separate segmented tube 82 configured to advance the inner tube 64 and stabilize the outer tube 62. The segmented tube 82 may include a plurality of articulating members or links 84 that act like puzzle pieces. The plurality of links 84 may be arranged in a generally linear configuration, as shown in FIG. 12, or may be curved, as shown in FIG. 13, for example, to mimic the shape of the outer tube 62.

Figure 12:
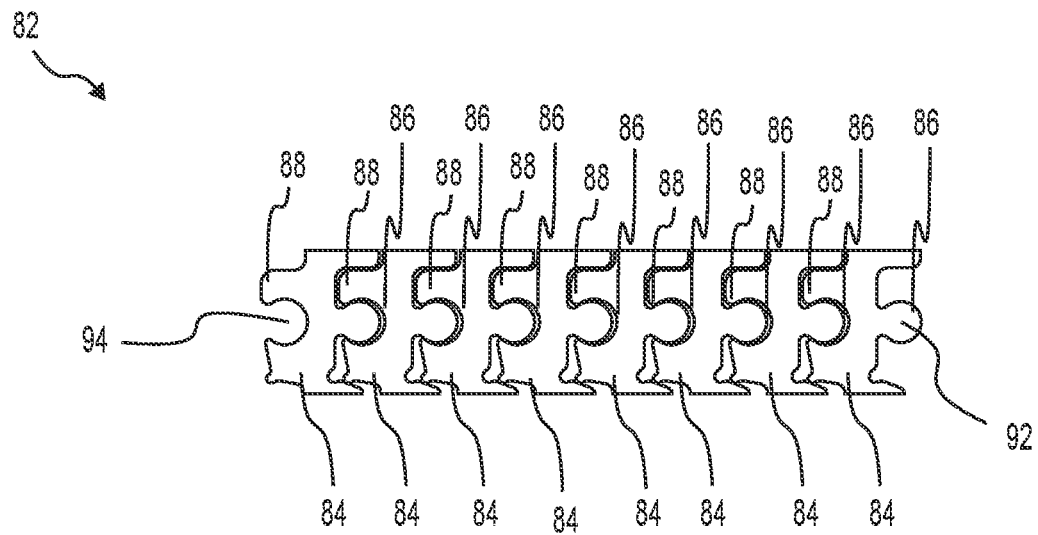
FIG. 12 is a close-up view of the segmented device with a plurality of links in a linear configuration.
Figure 13:
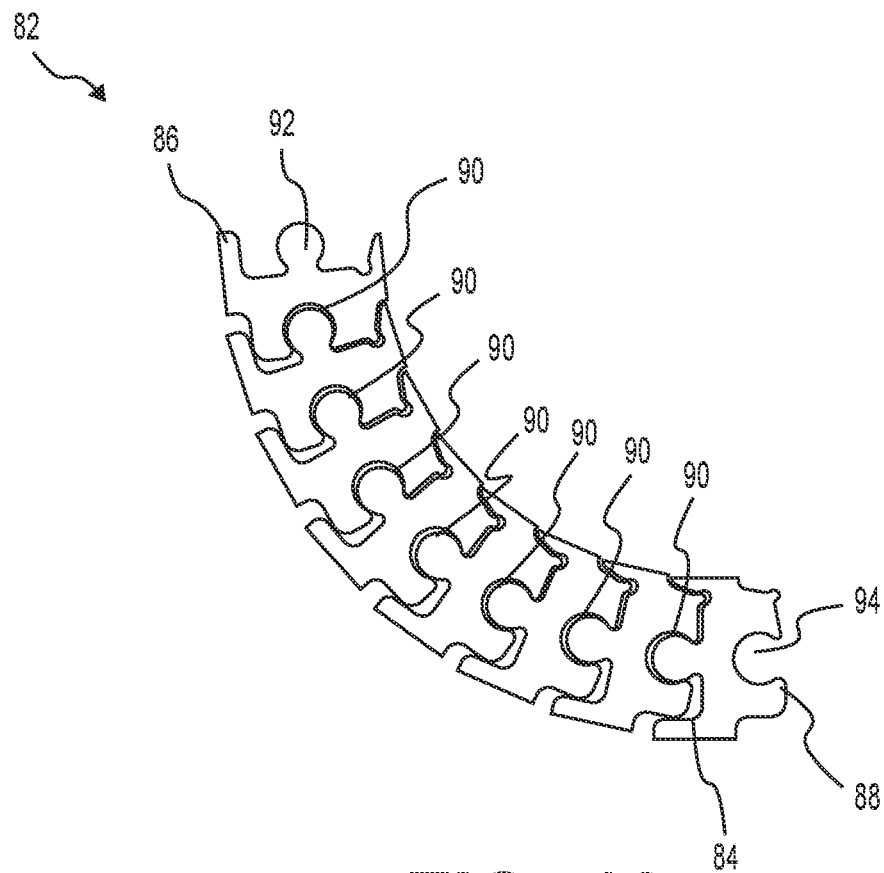
FIG. 13 is a close-up view of the segmented device with a plurality of links in a curved configuration.
Figure 14A:
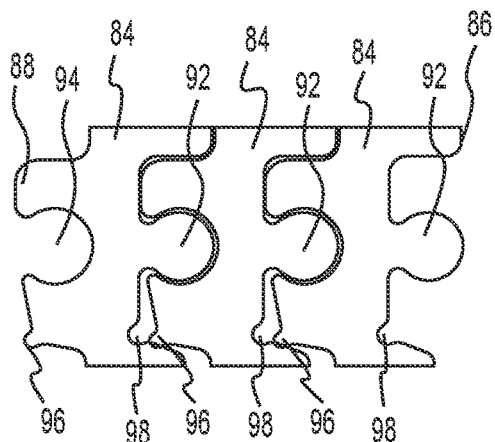
FIGS. 14A-14B are close-up views of a segmented device according to one embodiment.
Figure 14B:
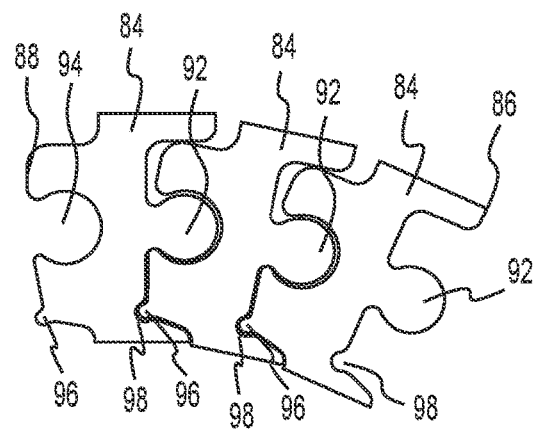
Figure 15A:
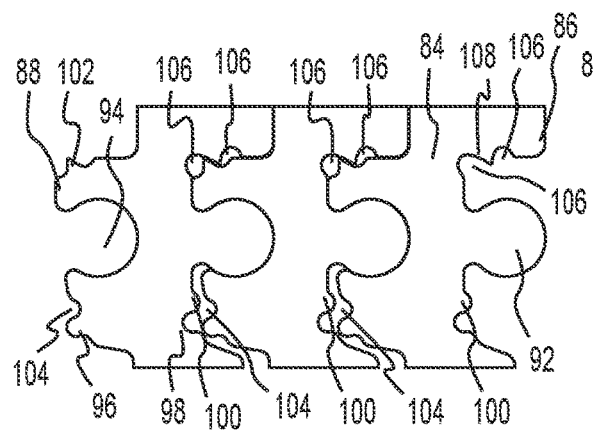
FIGS. 15A-15B are close-up views of a segmented device according to another embodiment.
Figure 15B:
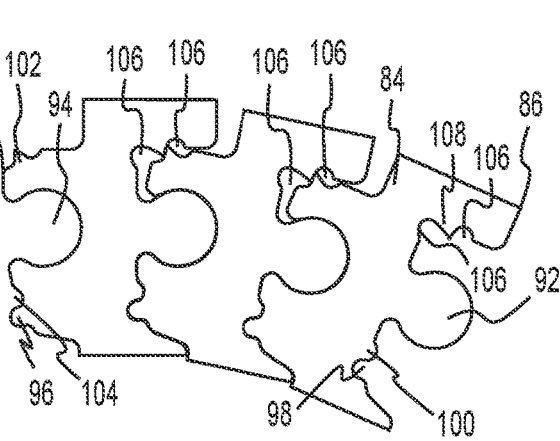
Figure 16A:
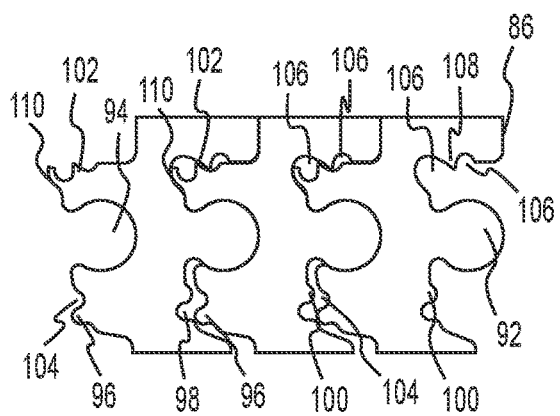
FIGS. 16A-16B are close-up view of a segmented device according to yet another embodiment.
Figure 16B:
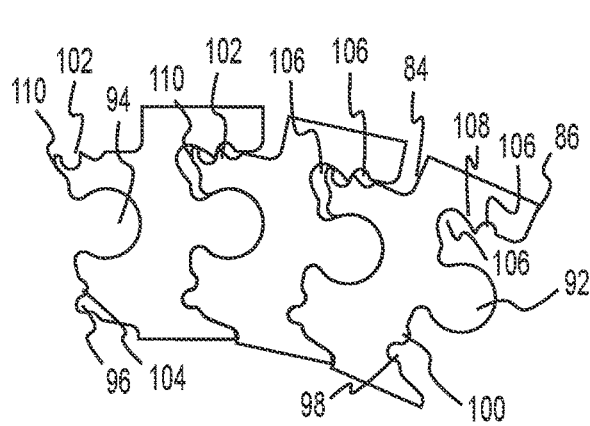

As best seen in FIGS. 12 and 13, each link 84 extends from a first end 86 to a second end 88. In this case, either the first end 86 or the second end 88 of a first link 84 may be inserted into the outer tube 62. In the embodiment shown, eight links 84 are connected such that the second end 88 of a given link 84 connects to the first end 86 of the next link 84 in the chain. Although it will be appreciated that any number of links 84 may be selected. Each of the links 84 are connected and able to articulate about a joint 90. In this embodiment, the first end 86 of each link 84 includes a ball 92 and the second end 88 of each link 84 includes a socket 94 configured to receive the ball 92 of an adjacent link 84. Accordingly, the socket 94 in the second end 88 of a given link 84 connects to the ball 92 of the first end 86 of the next link 84 in the chain. In this manner, each link 84 is able to articulate relative to the next link 84, thereby forming a curved segmented tube 82. Although a ball and socket joint 90 is exemplified in this embodiment, it will be appreciated that other suitable joints could be selected, such as pin joints, pivot joints, hinge joints or the like. It will also be appreciated that the locations of the ball 92 and socket 94 could be reversed on each link 84 or otherwise configured.

In one embodiment, the implant 80 may be installed as follows. The concentric curved tubes 62, 64 may be inserted into the pedicle 8 of the inferior vertebra 6. The articulatable puzzle pieces or links 84 of the segmented tube 82 may be impacted, for example, through a straight instrument connected to the proximal end 66 of the concentric tubes 62, 64. For example, the straight links 84 may be impacted one by one into the outer curved tube 62. The links 84 articulate and lock into a curved orientation during impaction. As additional links 84 are impacted, the inner tube 64 is incrementally advanced past the distal end 68 of the outer curved tube 62 and into the superior vertebral body 10. Thus, the segmented tube 82 drives the inner concentric tube 64 into the superior vertebral body 10. The segmented tube 82 may be configured to be encapsulated in the outer curved tube 62, thereby adding rigidity to the outer tube 62. If desired, bone cement may be injected through the concentric curved tubes 62, 64 and/or separately added to the superior vertebra 4 as described previously. In an alternative embodiment, if cement is not needed to be dispensed through the device 80, the segmented tube 82 may be solid and does not need to be hollow throughout.

Turning to FIGS. 14A-16B, alternative locking geometries may be used for the links 84, for example, to improve rigidity of the final construct. It will be appreciated that all of the links 84 for a given segment are shown identical, but it is envisioned that different links could be provided through the chain. In one embodiment shown in FIGS. 14A-14B, the second end 88 of the link 84 includes a protrusion or tab 96 configured to engage a corresponding recess 98 in an adjacent link 84. The tab 96 may be positioned, for example, below the socket 94 of the link 84 and the recess 98 may be positioned below the ball 92. In the straight configuration shown in FIG. 14A, the tabs 96 are not engaged with the recesses 98. In the curved configuration shown in FIG. 14B, the tabs 96 are locked in the respective recesses 98 of the adjacent links 84. In the embodiment shown in FIGS. 15A-15B, in addition to tab 96, a bump 100 is positioned above the recess 98 and an additional protrusion or spike 102 is provided. The bump 100 may be received in a corresponding recess 104 positioned adjacent to the tab 96, thereby further securing adjacent links 84 together. An upper portion of the second end 88 above the socket 94 may include a protrusion or spike 102, which is receivable in one or more corresponding notches 106 in the body of an adjacent link 84. In this manner, the spike 102 may act as a ratchet as it moves through one or more notches 106 as the links 84 articulate. In the curved configuration shown in FIG. 15B, the spike 102 may engage with a corresponding protrusion or spike 108 between two or more notches 106. In the embodiment shown in FIGS. 16A-16B, in addition to the features in FIGS. 15A-15B, the upper portion above the socket 94 may further includes a curved protrusion 110 adjacent to spike 100, which may be configured to further lock the link 84 to an adjacent link 84. For example, the protrusion 110 may be received in one of the notches 106 in the body of an adjacent link 184. One or more of the locking geometries may be used for one or more of the links 84, for example, to improve rigidity of the segmented tube 82.

Figure 17:
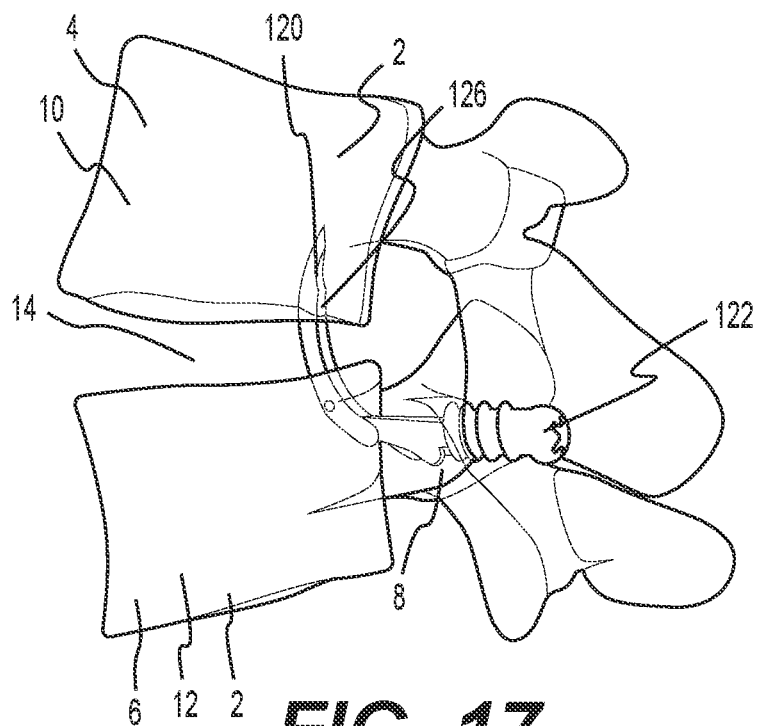
FIG. 17 is a lateral view of two adjacent vertebrae with a pedicle-based intradiscal fixation device implanted through the pedicle of the inferior vertebra and engaged with the vertebral body of the superior vertebra according to one embodiment.
Figure 18:
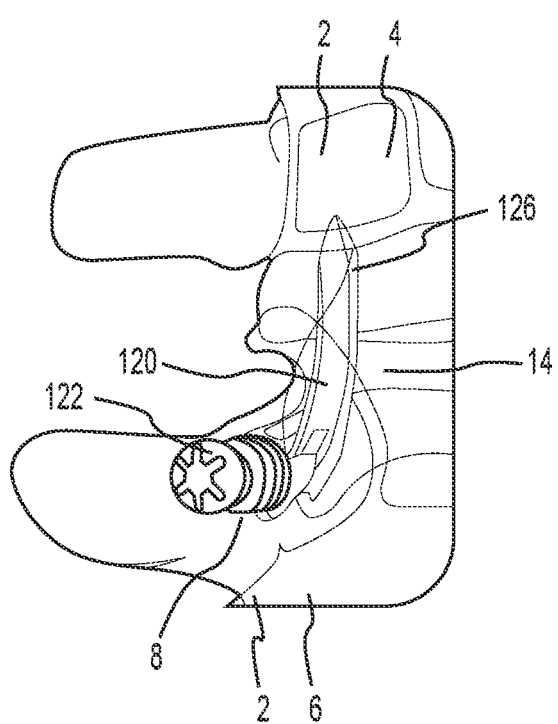
FIG. 18 is a posterior view of the vertebrae and pedicle-based intradiscal fixation device of FIG. 17.
Figure 19:
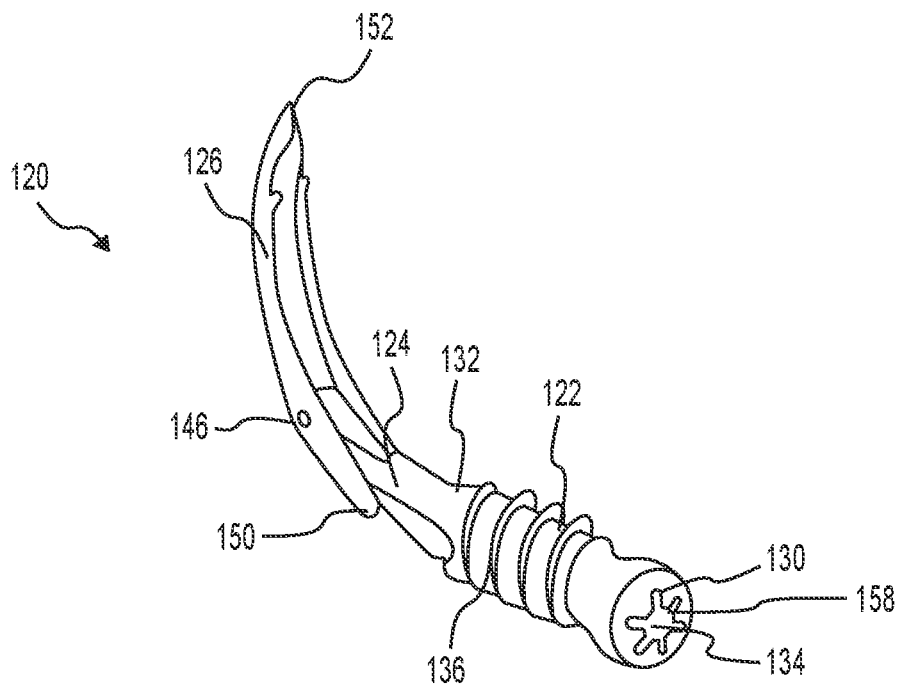
FIG. 19 is a perspective view of the pedicle-based intradiscal fixation device of FIG. 17 in an extended position.
Figure 20:
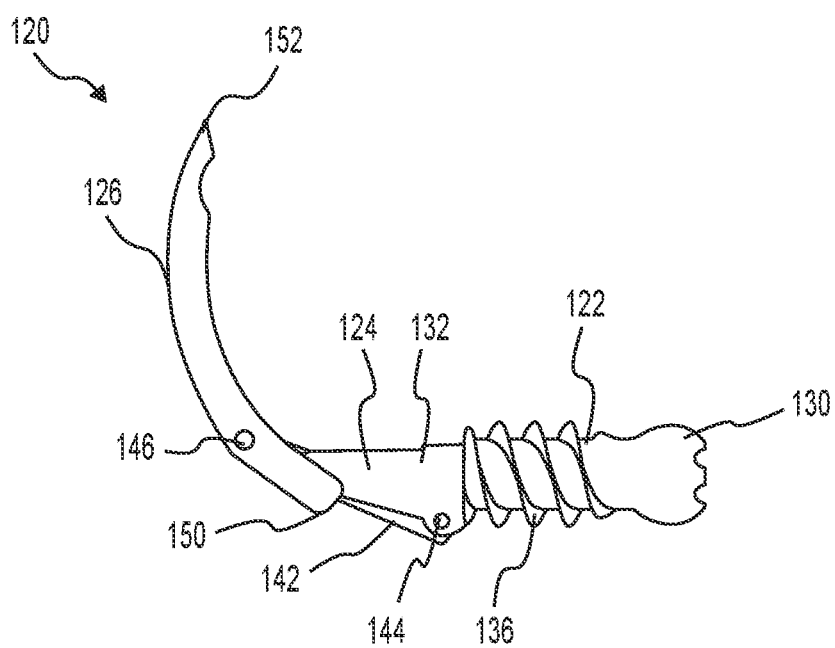
FIG. 20 is a side view of the pedicle-based intradiscal fixation device of FIG. 19 in the extended position.

Turning now to FIGS. 17 and 18, a pedicle-based intradiscal fixation device 120 according to another embodiment is shown. The method of fixation may be similar to the methods described herein for other devices. For example, the spine may be accessed posteriorly and the device 120 may be inserted into the pedicle 8 of the inferior vertebra 6 in a collapsed configuration. The device 120 may be further advanced into the vertebral body 12 of the inferior vertebra 6. The device 120 may then be expanded or extended into the vertebral body 10 of the adjacent superior vertebra 4. Thus, the device 120 may traverse the disc and/or disc space 14 between the two vertebrae 2.

Figure 21:
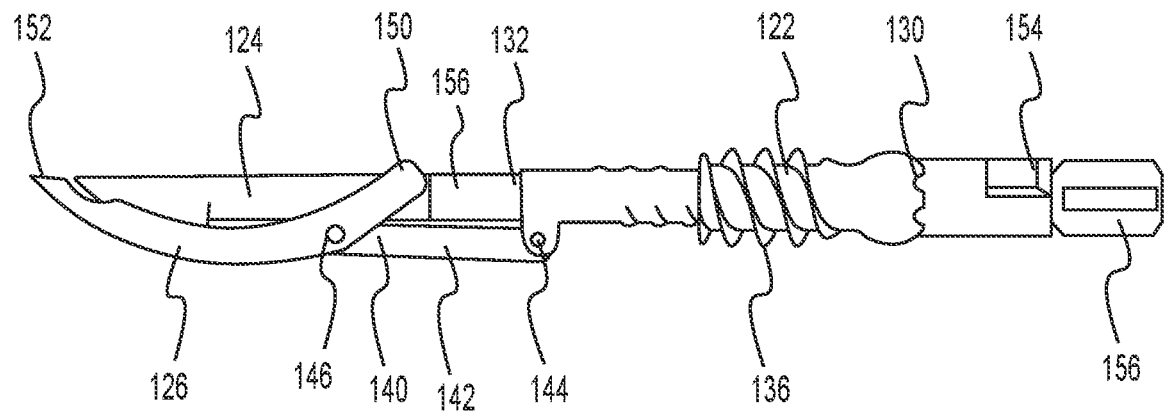
FIG. 21 is a side view of pedicle-based intradiscal fixation device of FIG. 19 in a collapsed position with a mechanism for extending the anchor portion.
Figure 22:
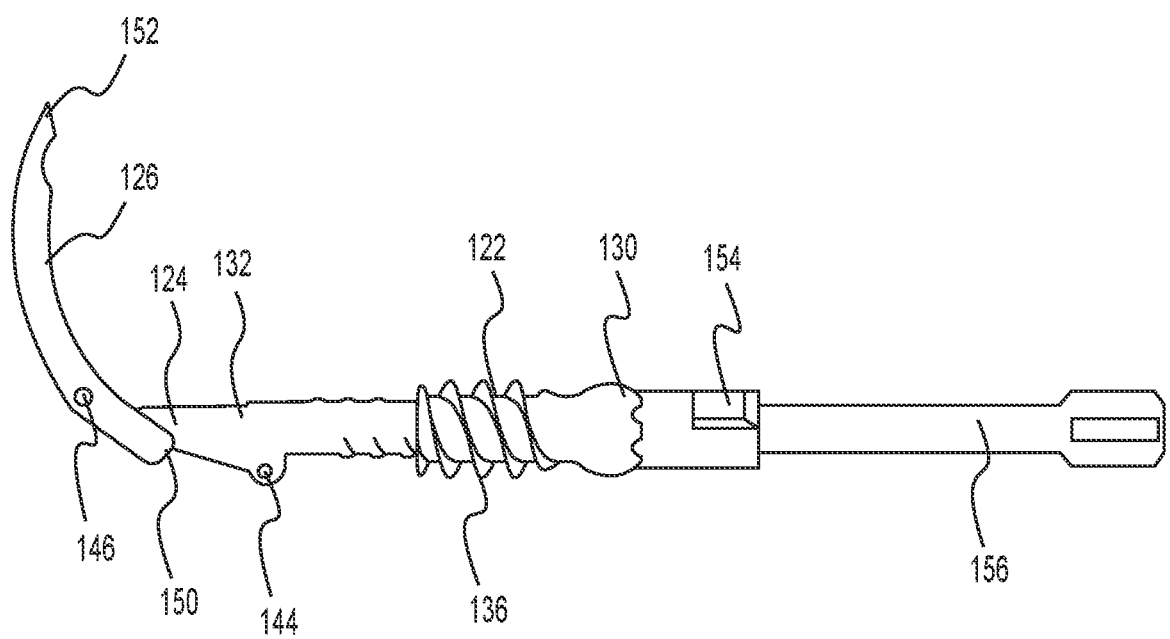
FIG. 22 is a side view of the pedicle-based intradiscal fixation device of FIG. 21 in an extended position with the mechanism extending the anchor portion.

Referring to FIGS. 19-22, the pedicle-based intradiscal fixation device 120 is shown in more detail. The pedicle-based implant 120 may include a screw portion 122 and an anchor portion 126 moveably connected to the screw portion 122. As best seen in FIG. 21, the implant 120 has a collapsed configuration, thereby allowing the implant 120 to be inserted into the pedicle 8 of the inferior vertebra 6, for example, in a minimally invasive manner. As shown in FIG. 22, once inserted in the inferior vertebra 6, the implant 120 has an expanded or extended configuration whereby the anchor portion 126 is extended outwardly, thereby allowing for the anchor portion 126 to be inserted into the superior vertebra 4.

The screw portion 122 may have a body extending from a first end 130 to a second 132. The first end 130 may be a proximal end and may include a recess 134 configured to receive an instrument for inserting the implant 120. The first end 130 may have an enlarged head portion or may be otherwise configured (e.g., headless). The second end 132 may be a distal end coupled to the moveable anchor portion 126. The screw portion 122 may be generally hollow and may be configured to slide along a rod portion 124. The body of the pedicle screw 122 may include one or more threads 136 along the entire length of the shaft or a portion thereof. The thread 136 may have a suitable angle, lead, pitch, etc. to enhance insertion and/or engagement with the bone. Although a threaded screw portion 122 is exemplified in this embodiment, it will be appreciated that it could be substituted with ribs, teeth, or other bone fixation mechanisms.

The anchor portion 126 may have a body extending from a first end 150 to a second end 152. The first end 150 may be a proximal end and the second end 152 may be a distal end configured to be inserted into the vertebral body 10 of the superior vertebra 4. The second end 152 may have a distal tip that is sharp, pointed, or otherwise configured to engage bone. The anchor portion 126 may be curved or otherwise contoured. The anchor portion 126 may have sufficient length such that the anchor 126 may span from the inferior vertebra 6 to the superior vertebra 4 through the affected disc space 14. In the extended position, the anchor portion 126 may be generally positioned perpendicular to the screw portion 122 or the anchor portion 126 may be angled or otherwise oriented to engage the vertebral body 10 of the superior vertebra 4.

As best shown in FIGS. 21 and 22, an articulation assembly 140 is configured to articulate the anchor portion 126 from the collapsed position to the extended position. The articulation assembly 140 may include a push rod 142 connected to the distal end 132 of the screw portion 122 by a first pin 144 and connected to the anchor portion 126 by a second pin 146. When the screw portion 122 moves forward along the rod portion 124, the push rod 142 pushes forward and slides the anchor portion 142 outward. The anchor portion 142 and rod portion 124 may include one or more corresponding tracks configured to facilitate the movement. An instrument 154 may be provided to articulate the anchor portion 142. For example, as shown in FIG. 21, the instrument 154 may be affixed to the head of the screw portion 122. An inner rod 156 of the instrument 154 may be inserted through the screw portion 122 and may couple to the rod portion 124 of the implant 120. When the screw portion 122 is moved forward along the inner rod 156 and the rod portion 124 and/or the inner rod 156 is withdrawn from the screw portion 122, the anchor portion 126 articulates outward into the extended position shown in FIG. 22. Once in its final extended position, one or more locking members may be used to lock the articulated implant 120, thereby facilitating resistance to toggle. For example, a threaded locking cap 158 may be inserted into the recess 134 of the implant 120 to lock the anchor portion 126 in the extended position.

Figure 23A:
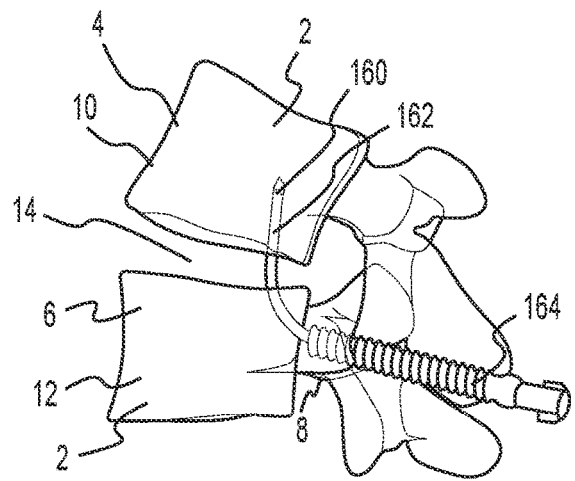
FIGS. 23A-23D provide lateral and posterior views, respectively, of two adjacent vertebrae with a pedicle-based intradiscal fixation device implanted through the pedicle of the inferior vertebra and engaged with the vertebral body of the superior vertebra according to one embodiment.
Figure 23B:
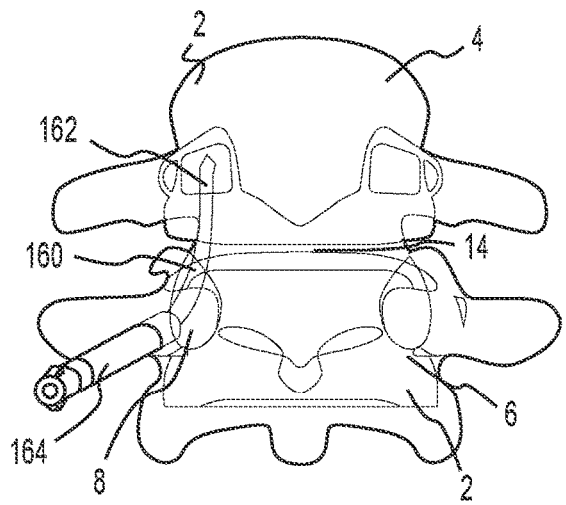
Figure 23C:
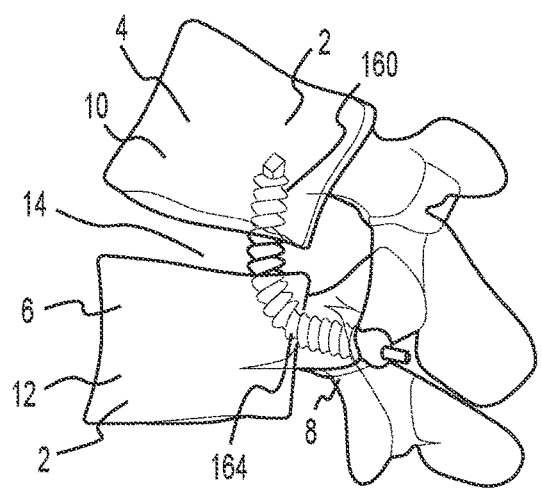
Figure 23D:
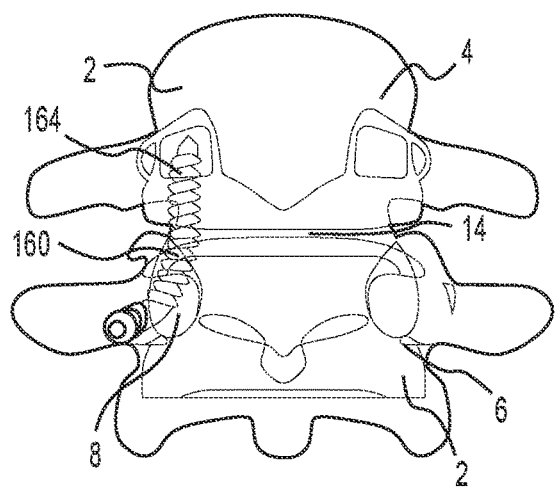

Turning now to FIGS. 23A-23D, a pedicle-based intradiscal fixation device 160 according to another embodiment is shown. The method of fixation may be similar to the methods described herein for other devices. For example, the spine may be accessed posteriorly and the device 160 may be inserted into the pedicle 8 of the inferior vertebra 6 in a first or initial configuration, shown in FIG. 23A. The device 160 may be further advanced into the vertebral body 12 of the inferior vertebra 6 and into the vertebral body 10 of the adjacent superior vertebra 4. Thus, the device 160 may traverse the disc and/or disc space 14 between the two vertebrae 2. The device 160 may be manipulated into a second or final configuration by positioning a flexible screw 164 over a curved nail 162, as shown in FIG. 23C.

Figure 24:
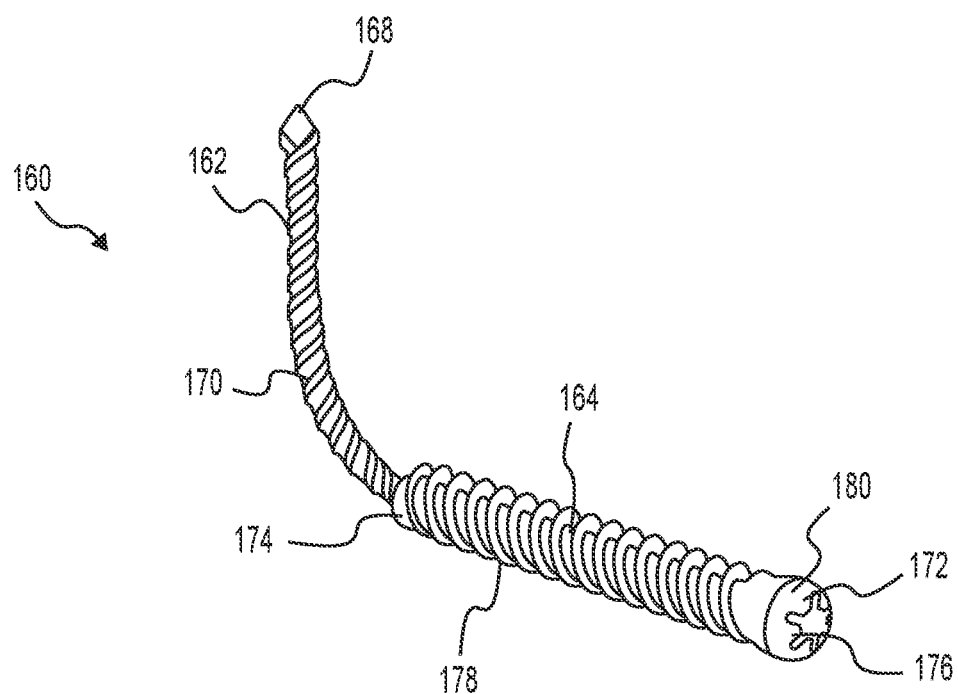
FIG. 24 is a perspective view of the pedicle-based intradiscal fixation device of FIGS. 23A-23D with the device in an initial position.
Figure 25:
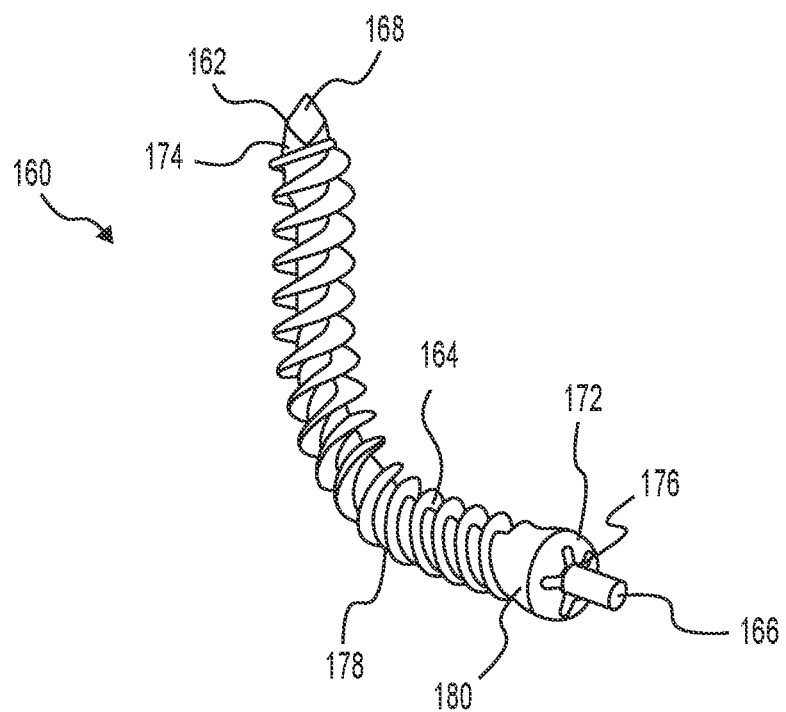
FIG. 25 is a perspective view of the pedicle-based intradiscal fixation device of FIG. 24 with the device in a final, installed position.
Figure 26A:
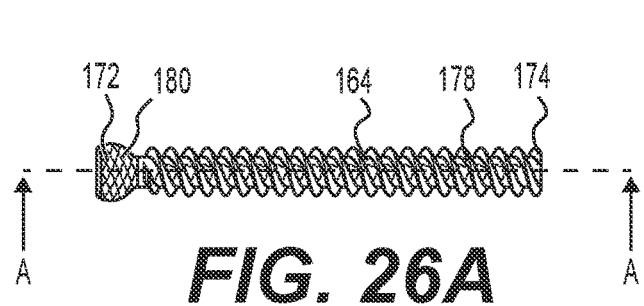
FIGS. 26A-26E provide alternative views of the flexible screw of FIG. 25.
Figure 26C:
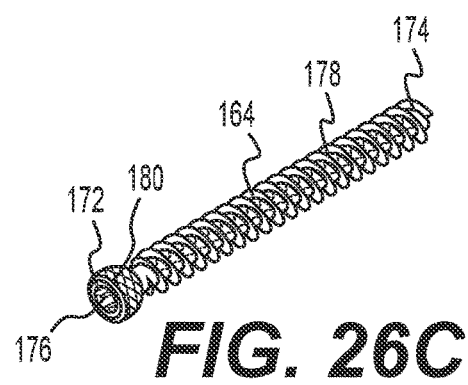
Figure 26B:
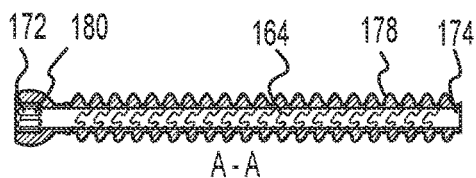
Figure 26D:
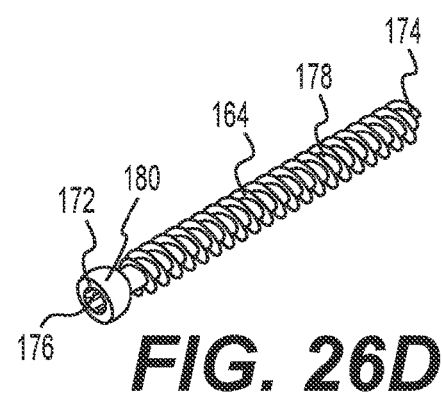
Figure 26E:
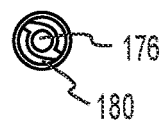
Figure 27A:
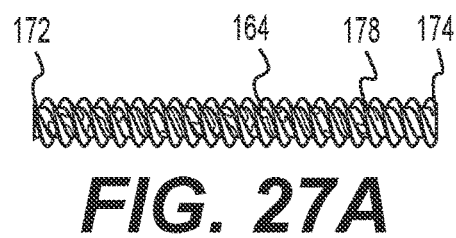
FIGS. 27A-27D provide alternative views of a flexible screw according to one embodiment.
Figure 27C:
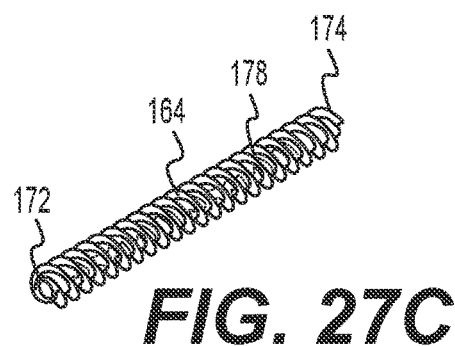
Figure 27B:
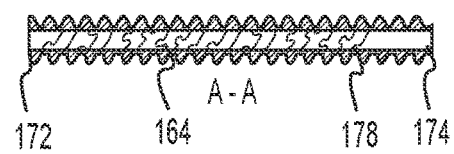
Figure 27D:
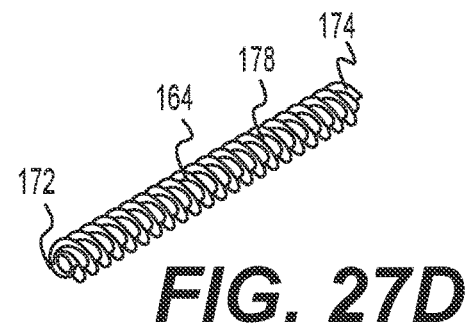
Figure 28A:
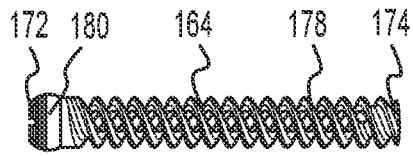
FIGS. 28A-28H provide alternative views of a flexible screw according to another embodiment.
Figure 28C:
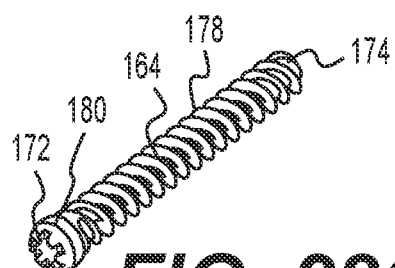
Figure 28B:
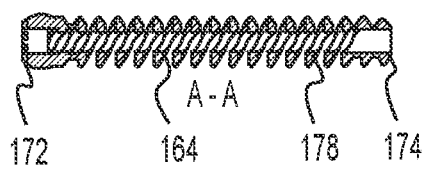
Figure 28D:
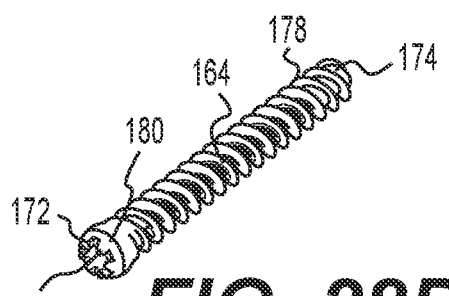
Figure 28E:
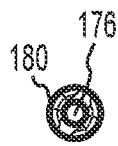
Figure 28F:
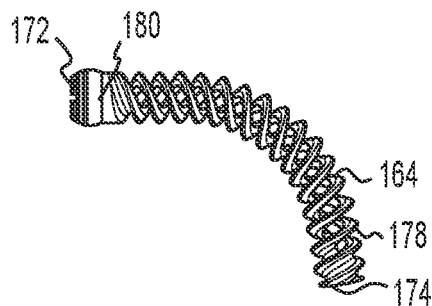
Figure 28H:
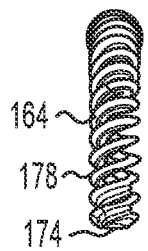
Figure 28G:
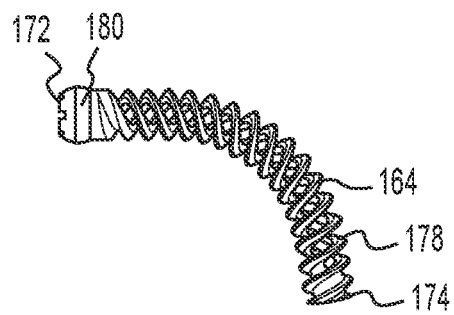
Figure 29A:
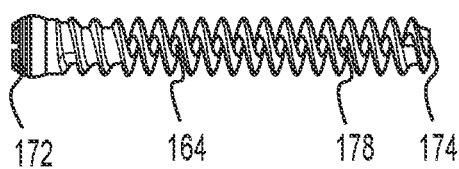
FIGS. 29A-29E provide alternative views of a flexible screw according to yet another embodiment.
Figure 29C:
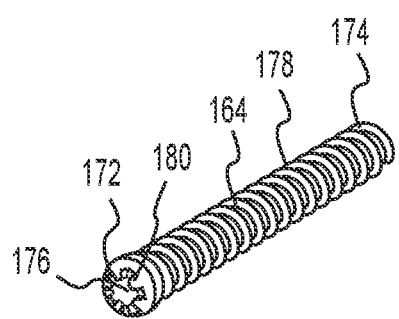
Figure 29B:
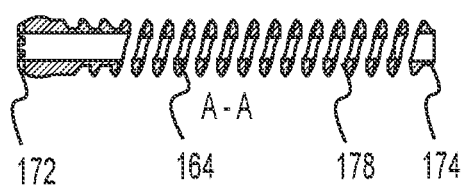
Figure 29D:
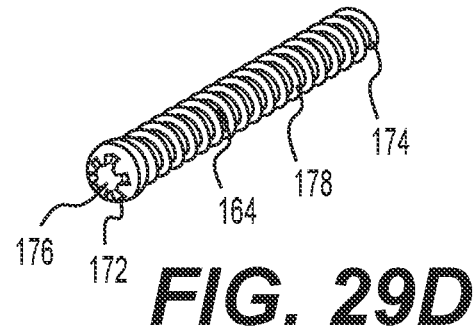
Figure 29E:

Referring to FIGS. 24 and 25, the pedicle-based intradiscal fixation device 160 is shown in more detail. The pedicle-based implant 160 may include a nail 162 and a screw 164 moveable along the length of the nail 162. As best seen in FIG. 24, the implant 160 has an initial configuration, whereby the nail 162 may be inserted into the pedicle 8 of the inferior vertebra 6, the vertebral body 12 of the inferior vertebra 6, and the vertebral body 10 of the superior vertebra 4. As shown in FIG. 25, the implant 160 has a final configuration whereby the screw 164 is inserted over the nail 162 to rigidly lock the segments and provide resistance to pullout.

The nail 162 may have a body extending from a first end 166 to a second end 168. The first end 166 may be a proximal end and the second end 168 may be a distal end configured to be inserted into the vertebral body 10 of the superior vertebra 4. The second end 168 may have a distal tip that is sharp, pointed, or otherwise configured to engage bone. The nail 162 may have one or more helical channels or grooves 170 configured to engage bone and/or facilitate movement of the screw 164 when inserted over the nail 162. In other words, the nail 162 may be threaded along its entire length or a portion thereof. The nail 162 may be curved or otherwise contoured along its length. For example, the nail 162 may have a first straight portion near the proximal end 166, a curved portion, and then a second straight portion near the distal end 168. The nail 162 may be sufficiently rigid such that it maintains its shape as the screw 164 is inserted thereon. The nail 162 may have a sufficient length such that nail 162 may span from the pedicle 8 to the inferior vertebra 6 and to the superior vertebra 4 through the affected disc space 14.

Alternative versions of the screw 164 are shown in FIGS. 26-29. The screw 164 may have a body extending from a first end 172 to a second 174. The first end 172 may be a proximal end and may include a recess 176 configured to receive an instrument for inserting the screw 164. As best seen in FIGS. 26A-26D, the first end 172 may have an enlarged head portion 180. Alternatively, as shown in FIGS. 27A-27D, the first end 172 may be headless. The second end 174 may have a distal tip that is blunt, pointed, or otherwise configured to engage bone. The screw 164 may be generally hollow and may be configured to receive the nail 162 therein. The screw 164 may be formed by one or more threads 178. The thread 178 may be an open helical spring with gaps between each of the crests of the thread 178. The thread 178 may have a suitable angle, lead, pitch, etc. to enhance insertion and/or engagement with the bone.

As best seen in FIGS. 28A-28H, the flexible screw 164 may have a generally linear or straight configuration and may be bent into a generally curved configuration. Due to the open geometry of the thread 178, the screw 164 may be flexible such that it is capable of bending easily to conform to the curved geometry of the nail 162. Accordingly, after the threaded curved nail 162 is inserted into the inferior pedicle 8 through to the superior vertebral body 10, spanning the intradiscal space 14, the flexible screw 164 may be threaded over the threaded curved nail 162 to rigidly lock the segments and provide resistance to pullout.

Iatrogenic adjacent segment disease and other surgical issues have been attributed to pedicle screw fixation previously. This intradiscal fixation devices and methods described herein may obviate the need for pedicle screw fixation while potentially avoiding their iatrogenic effects. Traditional techniques may require multiple incisions for even minimally invasive pedicle screw fixation. The pedicle-based intradiscal fixation devices described herein may provide better stability in flexion, extension, and/or axial rotation compared with other anchor type fixation methods used in the anterior or lateral approaches. Compared with an anterior/lateral anchor or screw and plate method, the pedicle-based intradiscal approach may be performed from a posterior approach, avoiding potential disruption of vasculature or nerve roots found in the anterior and/or lateral approaches.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. An implant for stabilizing an inferior vertebra and a superior vertebra, the implant comprising:
    an outer tube defining a central longitudinal axis, the central longitudinal axis curved along its length defining a second central longitudinal axis, the second central longitudinal axis curved along its length, positionable within the outer tube, wherein the implant has a collapsed position whereby the inner tube is positioned inside the outer tube, and the implant has an extended position whereby the inner tube extends from the outer tube,
    a separate segmented tube configured to advance the inner tube and stabilize the outer tube,
    wherein the outer tube is configured to be inserted through a pedicle of the inferior vertebra in the collapsed position, and the inner tube is configured to engage bone of the superior vertebra in the extended position,
    wherein the inner tube is configured to be incrementally advanced past a distal end of the outer curved tube and into the superior vertebral body,
    wherein the segmented tube is configured to drive the inner tube into the superior vertebral body.

2. The implant of claim 1, wherein the inner tube has one or more ribs extending along the length of the tube.

3. The implant of claim 1, wherein the outer and inner tubes are hollow.

4. The implant of claim 1, wherein the segmented tube includes a plurality of articulating links.

5. The implant of claim 4, wherein each of the links includes a ball and a socket configured to receive the ball of an adjacent link.

6. The implant of claim 1, wherein the segmented tube is encapsulated by the outer tube in the extended position.

* * * * *